United States Patent
Federici et al.

(10) Patent No.: US 7,105,820 B2
(45) Date of Patent: Sep. 12, 2006

(54) TERAHERTZ IMAGING FOR NEAR FIELD OBJECTS

(75) Inventors: John F. Federici, Westfield, NJ (US); Dale E. Gary, Berkeley Heights, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 48 days.

(21) Appl. No.: 11/037,507

(22) Filed: Jan. 18, 2005

(65) Prior Publication Data

US 2006/0054824 A1  Mar. 16, 2006

Related U.S. Application Data

(60) Provisional application No. 60/560,664, filed on Apr. 8, 2004, provisional application No. 60/537,076, filed on Jan. 16, 2004.

(51) Int. Cl.
*G01J 5/02* (2006.01)
(52) U.S. Cl. ................................. 250/339.02
(58) Field of Classification Search ............ 250/339.02
See application file for complete search history.

(56) References Cited

U.S. PATENT DOCUMENTS

| | | | |
|---|---|---|---|
| 5,623,145 A | 4/1997 | Nuss | |
| 6,180,945 B1 * | 1/2001 | Barton et al. | 250/370.1 |
| 6,242,740 B1 * | 6/2001 | Luukanen et al. | 250/353 |
| 6,777,684 B1 * | 8/2004 | Volkov et al. | 250/341.1 |
| 6,815,683 B1 | 11/2004 | Federici et al. | |
| 6,853,707 B1 * | 2/2005 | Kerschner | 378/98.8 |
| 2005/0122249 A1 * | 6/2005 | Grudkowski et al. | 342/22 |

OTHER PUBLICATIONS

John F. Federici et al., "Terahertz near-field imaging", Institute of Physics Publishing, Physics in Medicine and Biology, Phys. Med. Biol. 47 (2002), pp. 3727-3734.
John F. Federici, et al., "Terahertz imaging using an interferometric array", Applied Physics Letters, vol. 83, No. 12, Sep. 22, 2003, pp. 2477-2479.

* cited by examiner

*Primary Examiner*—David Porta
*Assistant Examiner*—Marcus Taningco
(74) *Attorney, Agent, or Firm*—Gregory C. Ranieri

(57) ABSTRACT

Near field imaging using a THz imaging system is realized by utilizing an interferometric imaging detector array that includes detector elements disposed on a surface curved, physically or artificially, to match substantially the curvature of the wave front for received THz signals. Generally, the near field is an environment wherein the distance to an object of interest is on the order of 10–100 times larger than the physical size of the THz imaging array. Typical distances from the object or target to the imaging array is anticipated to be in the 0.5 m–50 m range. Curvature of the detector array corrects a distortion problem in prior THz imaging systems that utilized planar interferometric imaging arrays based on a planar wave front assumption for received THz signals.

21 Claims, 9 Drawing Sheets

ARRANGEMENT OF ANTENNAS IN ARRAY

5 ANTENNAS IN LINE: COORDINATES: 0, 1A, 3A, 7A, 16A
PROVIDES BASELINES: 1, 2, 3, 4, 6, 7, 9, 13, 15, 16 x a (a)

(b)

(a)

(b)

(a)

(b)

TERAHERTZ IMAGING FOR NEAR FIELD OBJECTS

CROSS-REFERENCE TO RELATED APPLICATION

This application claims the benefit of priority from both U.S. Provisional Patent Application Ser. No. 60/537,076 filed on Jan. 16, 2004 and U.S. Provisional Patent Application Ser. No. 60/560,664 filed on Apr. 8, 2004. Each of the above applications is incorporated by reference herein in its entirety.

GOVERNMENT RIGHTS

The United States government may have certain rights in this invention. A portion of the work described herein was supported by the U.S. Army through an STTR Contract DAAD19-02-C-0085 and an SBIR Contract DAAD19-03-C-0137. Also, a portion of the work described herein was supported by the United States Technical Support Working Group (TSWG-ED) under Grant N41756-04-C-4163.

BACKGROUND OF THE INVENTION

1. Field of the Invention

This invention relates to imaging apparatus and methods and, more particularly, to Terahertz or T-ray imaging systems and methods which utilize electromagnetic radiation in the Terahertz (THz) range as incident energy upon objects under examination.

2. Description of the Related Art

Terahertz (THz) or T-ray imaging systems have been developed to monitor, detect, and recognize the presence of certain materials or objects that are introduced to the field of view for the imaging system. These systems operate in a non-destructive and non-invasive manner. They have been suggested for applications including process control, materials inspection, biomedical imaging, fault detection in materials, material profiling, and packaging inspection, to name but a few. A description of one such imaging system is given in U.S. Pat. No. 5,623,145 issued to M. Nuss. In this description, the terms "Terahertz imaging", "T-ray imaging", and "THz imaging" are used interchangeably without any intended change or loss in meaning.

Recently, the need has increased to be able to detect and identify, both quickly and reliably, concealed explosives and other chemical and biological agents as these items increasingly become weapons of war and terrorism. Terahertz systems have been proposed for this task using their characteristic transmission or reflectivity spectra in the THz range (approximately 0.1 THz–10 THz). Explosives such as C-4, HMX, RDX, TNT, and naphthalene all have characteristic reflection and absorption spectra in the 0.1–2.0 THz range (corresponding wavelength range of 3 mm–0.15 mm). These materials are easily distinguishable from other non-hazardous materials such as human skin. In essence, explosives appear as different "colors" to the THz detector as compared to non-hazardous items. The same principles apply to THz detection and imaging of agents used in chemical and biological weapons.

By using THz spectroscopy and imaging, it is therefore possible to detect and identify explosives and other chemical and biological weapons, even when they are concealed in clothing, sealed packages, suitcases, or the like, because the THz radiation is readily transmitted through concealment materials such as plastics, clothing, luggage, paper products, walls, and other insulative (i.e., non-conductive or non-metallic) materials. Identification of these agents is accomplished by comparing the spectra measured for the reflected or transmitted THz signals with known calibration spectra. These spectra are substantially unique signatures that distinguish the agents from other objects such as keys, coins, human skin, and clothing. Since metals are relatively opaque to transmission of THz wavelengths and exhibit substantially constant reflection spectra, weapons such as handguns and knives are similarly identifiable by THz imaging techniques.

THz imaging systems proposed in the past have been based upon a single THz source and THz detector pair that are synchronously scanned transversely across the object being imaged in order to generate the two dimensional image. These systems consequently take a significant amount of time to acquire sufficient data and thereby generate the image of even a single small object. As a result, they are not suitable for applications that depend on real-time acquisition of THz images.

Current THz imaging is based on using a single THz source such as a short-pulsed laser or multiple continuous wave sources whose output signals are combined to produce the required THz difference frequency. One difficulty with extending either of these techniques to continuous wave THz imaging of coherent or incoherent THz radiation is that coherent continuous wave or short-pulsed laser sources are required. Moreover, a coherent phase relationship is needed between the laser sources that generate and that detect the THz signals. But imaging of an incoherent THz source is not possible through the use of any of these methods.

In U.S. Pat. No. 6,815,683 issued to J. Federici et al. on Nov. 9, 2004, THz imaging apparatus and methods are disclosed by the inventors herein for rapid and effective examination of a region of interest to detect the presence of certain compositions. This design and technique does not require a particular coherent or incoherent source of THz signals. Instead, it allows the flexibility to choose any source such as an electronic THz source, a laser-based THz illuminating source, or an incoherent ambient THz radiation which might be present, for example, from the sun. This system incorporates a substantially planar Terahertz (THz) Interferometric Imaging Arrays (TIIA) for remote-sensing applications. In utilizing such an array, it is generally assumed that the object of interest is sufficiently far enough away from the array that the incoming THz signal presents a substantially planar wave front.

The assumption about a planar wave front is reasonable for far field imaging. But it is does not hold for near field imaging. In near field applications, it should be understood that the wave front is curved and not planar. Therefore, the system described above would suffer inaccuracy in the detection and imaging of objects in the near field. Techniques have not been proposed to date to deal with the problem presented by curved wave fronts experienced when trying to apply the far-field THz imaging systems to the near-field imaging application.

SUMMARY OF THE INVENTION

Near field imaging using a THz imaging system is realized in accordance with the principles of the present invention by utilizing an interferometric imaging detector array that includes detector elements disposed on a surface curved to match substantially the curvature of the wave front for received THz signals. Generally, the near field is an environment wherein the distance to an object of interest is on the order of 10–100 times larger than the physical size of the THz imaging array. Typical distances from the object or target to the imaging array is anticipated to be in the 0.5 m–50 m range. Curvature of the detector array corrects a distortion problem in prior THz imaging systems that utilized planar interferometric imaging arrays based on a planar wave front assumption for received THz signals.

In one embodiment of the invention, the THz imaging detector includes an interferometric detector array having a plurality of individual detector elements disposed over a spherical surface thereby substantially matching the spherical curvature on the received THz signal wave front in the near-field. A radius of curvature approximately equal to the actual near field distance or an average near-field distance from the detectors to the object of interest can be employed for the spherical surface.

In another embodiment of the invention, the THz imaging detector includes an interferometric detector array having a plurality of detector elements disposed over a spherical surface exhibiting an adjustable radius of curvature that can be made to be approximately equal to the actual near-field range from the detectors to the object of interest. The THz imaging detector also includes a range detector and a controller, wherein the range detector acquires the range or distance from the detector elements to the object of interest or target and supplies that information to the controller and wherein the controller responds to the range information to controllably adjust the radius of curvature of the spherical surface.

In yet another embodiment of the invention, the THz imaging detector includes an interferometric detector array having a plurality of detector elements disposed over a detector surface, a range detector, and a controller. The range detector acquires the range or distance from the detector to the object of interest or target and supplies that information to the controller. In turn, the controller responds to the range information by controllably delaying each signal output from each detector element by a predetermined amount so that, when observed at a particular time instant, the detector element output signals represent signals detected from substantially the same wave front of the received THz signal from the target. In other words, the introduction of delay effectively adjusts the radius of curvature of the surface on which the detector elements reside so that the surface curvature is substantially matched to the curvature of the received THz signal wave front.

In other embodiments of the invention, the plurality of detector elements is disposed in a variety of different patterns including a circular pattern a random pattern in which the elements are dispersed at varying distances from each other, and a regular rectangular grid-like pattern in which the elements are located at the corners of a rectangle.

Additionally, the detectors can be disposed logarithmically along two orthogonal axes of the detector surface, whether planar or non-planar. In this latter embodiment, the detector surface is rotated by a predetermined amount about an axis normal to the two orthogonal axes and through their intersection. At each interval of rotation and until a full rotation (360°) is completed, THz signals are received from the target location and combined to form an image of the target. In this way, a detector array having relatively few detector elements can produce an imaging result comparable to an array having considerably more detector elements.

BRIEF DESCRIPTION OF THE DRAWINGS

A more complete understanding of the invention may be obtained by reading the following description of specific illustrative embodiments of the invention in conjunction with the appended drawings in which.

Figure 1:
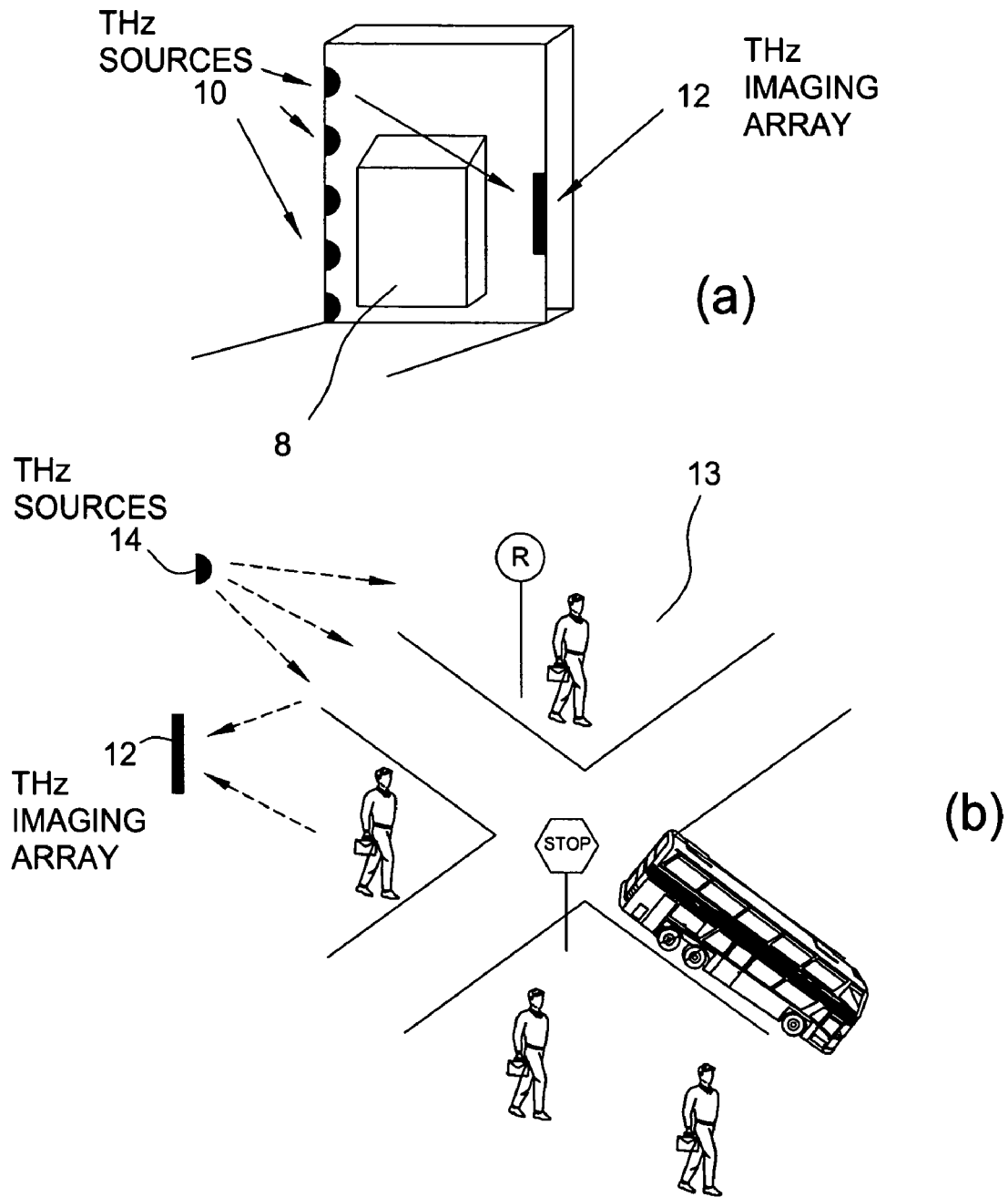
FIGS. 1a and 1b show simplified schematic drawings of illustrative embodiments of the present invention.

It is to be noted, however, that the appended drawings are not drawn to scale, are intended to illustrate only typical embodiments of this invention and are therefore not to be considered limiting of its scope, for the invention may admit to other equally effective embodiments. Where possible, identical reference numerals have been inserted in the figures to denote identical elements.

DETAILED DESCRIPTION

Overview of Imaging System

Terahertz (THz) imaging systems generally include two major components, namely, a THz transmitter or source and a THz receiver including an imaging array. These two components can be disposed either as shown in FIG. 1a for THz signal transmission through a target 8 or as shown in FIG. 1b for THz signal reflection by a target 13. The THz transmitter generates electromagnetic radiation at a desired THz frequency suitable for the imaging process and directs the radiation at the object or region of interest, which is also known as the target. The THz receiver includes both an imaging array comprised of a plurality of detector elements disposed on a surface to receive the THz signals from the target, via transmission or reflection, and a signal processor that converts the received THz signals into an image of the target from which the presence of specified compositions can be determined. This image is typically a frequency domain signature of the target that can be classified into, or matched against, known signatures or images in order to identify the target as a particular substance or composition.

A database of required THz-frequency spectral signatures for targets of interest, such as explosives, is provided for use with the signal processing system. Pattern matching or spectral matching is realized via content addressable memory systems, neural network algorithms, special purpose processors or the like to assist in the identification of selected targets from the THz images. Detailed explanations of prior exemplary THz imaging systems are included in U.S. Pat. Nos. 6,815,683 and 5,623,145, both of which are identified above and incorporated by reference herein in their entirety.

For non-intrusive, non-destructive screening of personnel, packages, or pallets entering an airport terminal, base, ship, or post office, personnel or packages shown as element 8 can be positioned between or move between a THz source or sources 10 and a THz imaging array 12 of a THz receiver. Alternatively, THz source 14 can illuminate spaced apart personnel and objects 13 so that imaging array 12 can detect THz signals reflected thereby. In both cases depicted in FIGS. 1*a* and 1*b*, the THz sources illuminate the person, pallet, vehicle or other object under study and the THz imaging array in the THz receivers detect the signals emanating from the targets so that the target data can be processed and identified using the signal processor in the receiver.

For routine, stand-off sensing, a wide area is illuminated with a bright THz source. The source can be broadband and incoherent such as radiation from the sun, or it can narrowband and tunable such as laser radiation. Received THz signals, whether reflected by or transmitted through the target area, are then detected by the THz imaging array. The THz receiver employed herein contains a priori information about the spectral content and location of the sources and seeks to determine the THz transmission or reflection properties of the intervening objects or targets.

The interferometric imaging technique, which is described in more detail in the '683 patent identified above, is utilized to image targets using THz signals in real time. According to this technique, signals received at two or more points in the aperture plane of the imaging array are combined together with the proper delay and correlated, using both in-phase and quadrature components, to transform the signals into the frequency domain while maintaining their spatial relationship on the plane. The need for delay will be described in more detail below. This technique measures both amplitude and phase of the received signals. When these measurements are made from a sufficient number of points in the aperture plane, an image of the original brightness distribution of the target can be synthesized by Fourier methods using standard inverse Fourier transforms. Raw images of the target after inversion can then be improved through standard image reconstruction techniques to reduce ambiguities (also called sidelobes) in the images. Exemplary reconstruction techniques that are well known in the art and useful in this regard are the CLEAN and Maximum Entropy Method (MEM) software packages. The CLEAN method will be discussed briefly below.

The basic CLEAN method was developed by Högbom in 1974. See J. Högbom, *Astronomy & Astrophysics J. Suppl.*, Vol. 15, pp. 417–26 (1974). It was originally designed for point sources, but it has been found to work well for extended sources as well when given a reasonable starting model. It is an iterative algorithm which deconvolves a sampling function (the "dirty beam") from an observed brightness ("dirty map") of a radio signal source. The CLEAN algorithm is of fundamental importance in radio astronomy, where it is used to create images of astronomical sources which are observed using arrays of radio telescopes ("synthesis imaging"). As a result of the algorithm's importance to synthesis imaging, a great deal of effort has gone into optimizing and adjusting the algorithm. CLEAN is a nonlinear algorithm, since linear deconvolution algorithms such as Wiener filtering and inverse filtering are inapplicable to applications with invisible distributions (i.e., incomplete sampling of the spatial frequency plane) such as maps obtained in synthesis imaging. Other versions of the CLEAN method are also known in the art.

An advantage of interferometric imaging compared to imaging with the equivalent of a digital camera is that interferometric imaging can be done with only a few individual detector elements. Megapixel and other comparable dense imaging array structures common in digital photography are presently not technologically feasible for use in the THz range because conventional THz detectors operating in the 0.1 THz–10 THz frequency range generally require liquid Helium cooling. In order to perform imaging in the THz range, one must be able to generate images using relatively few (e.g., 1–25) detector elements. In this application, interferometric imaging stands out because it offers the ability to image with a small number of detector elements. Moreover, interferometric imaging also offers the ability to image many sources of THz radiation at once, to image incoherent as well as coherent sources, and to provide spectral information as well as spatial imaging information about the object of interest.

Constructing images with interferometric arrays is a technique that has been developed for use with astronomical imaging in both the radio and X-ray wavelength ranges. The radio range, from metric to sub-mm wavelengths, has been the traditional regime for development of the techniques of Fourier image reconstruction. Sparse arrays containing relatively few detectors, such as 3–10 detector elements, require special treatment to reduce ambiguities known as sidelobes in reconstructed images. When applying the interferometric imaging technique in the Terahertz (THz) and Gigahertz (GHz) frequency ranges for imaging targets such as concealed weapons and explosives, the prior art systems of THz Interferometric Imaging Arrays (TIIA) for remote-sensing applications generally assumed that the target is far enough away from the imaging array that the incoming THz wave fronts are planar. That is, in prior art THz imaging systems, the curvature of the incoming wave fronts has been neglected. But for the present invention in near field applications, typical distances from a target or group of targets to the imaging array may be on the order of 0.5 m–50 m. At this range, the curvature of the wave front cannot be neglected. Rather than parallel incoming THz wave fronts assumed in far field applications, the wave fronts in this near field application are curved as they impinge on the imaging array.

Receiver Configuration

Figure 13:
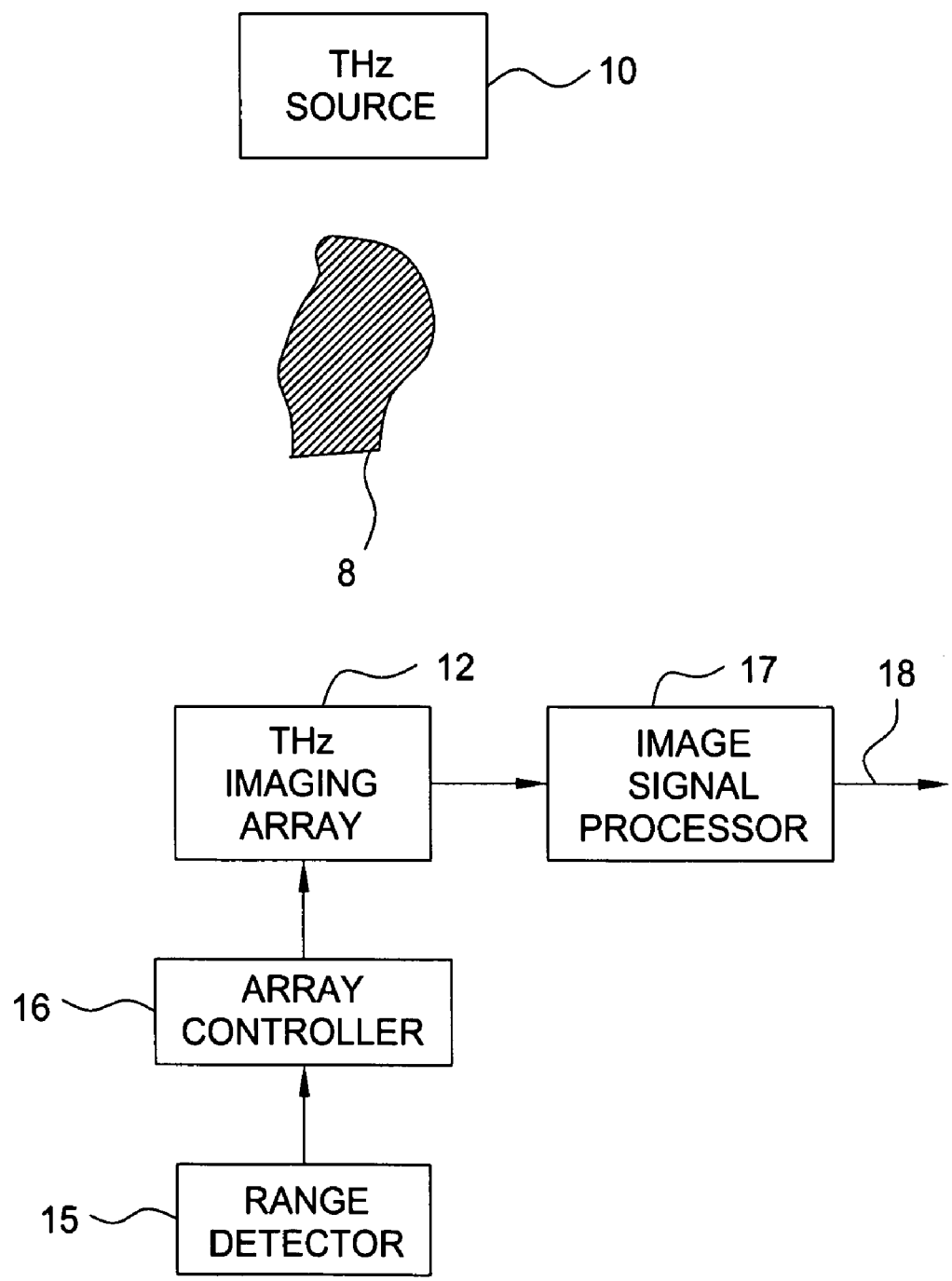
FIG. 13 shows a simplified block diagram of another embodiment of the terahertz imaging system.

While most of the attention in this description is intended to be directed to improvements in the imaging array for near field THz imaging applications, it is important to understand the overall THz receiver configuration. To that end, examples of THz imaging receivers suitable for use with the present invention are shown in simplified block diagram form in FIGS. 2, 3 and 13. These embodiments will be briefly described below.

In THz imaging apparatus described above, the receiver includes a tunable interferometric array of spaced-apart detector elements, also known as THz antennae. Signal outputs from pairs of the detectors are combined using well known techniques with proper delay and correlation of in-phase and quadrature signal components to produce components for the Fourier transform plane (u-v plane) corresponding to the detector plane. For example, dual correlation of the detected signals together with the use of a π/2 phase shift for one of the detected signals in the pair can allow both sine and cosine components to be measured simultaneously. These components become the complex visibility at spatial frequency (u, v) corresponding to the projected baseline between the two detectors in that pair.

As described above, the THz imaging receiver includes an array of individual detectors. Each detector measures the amplitude and phase of incoming THz radiation. As a wave front of THz radiation encounters the array, each pair of detectors (known as a baseline pair) measures one spatial Fourier component of the incoming THz signal as determined by the separation of the detector pair, otherwise known as the baseline. Each spatial Fourier component is represented by a point in the Fourier transform plane, known as the u-v plane. In order to determine a spatial Fourier component and consequently the direction of the incoming THz wave front, the delay in arrival time of the same wave front between a pair of antennas must be measured. For a target emanating THz signals, this measurement will yield an angle α at which the target is located from the detector. In order to image the target, additional measurements with baselines at other spacings and orientations must be carried out.

For a given number of detectors N, there are $N(N-1)/2$ possible baseline pair combinations available. An image is generated from the spatial Fourier components of all the different baseline pair combinations. The quality of an image depends on the ultimate coverage for this data over the u-v plane, which in turn depends on the arrangement of the detecting elements of the interferometer. A primary concern in designing the configuration of detecting elements (antennas) is to obtain uniform and efficient coverage of the u-v plane over a range determined by the required angular resolution.

Figure 11:
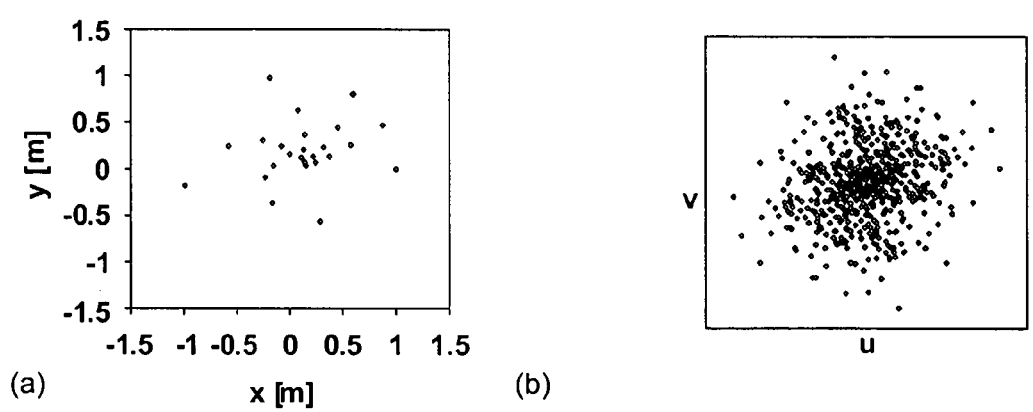
FIGS. 11a, 11b, 12a, and 12b are additional schematic diagrams and their distribution points in the u-v plane for detector element (antenna) layout patterns for use in a THz interferometric detector realized in accordance with the principles of the present invention.
Figure 12:
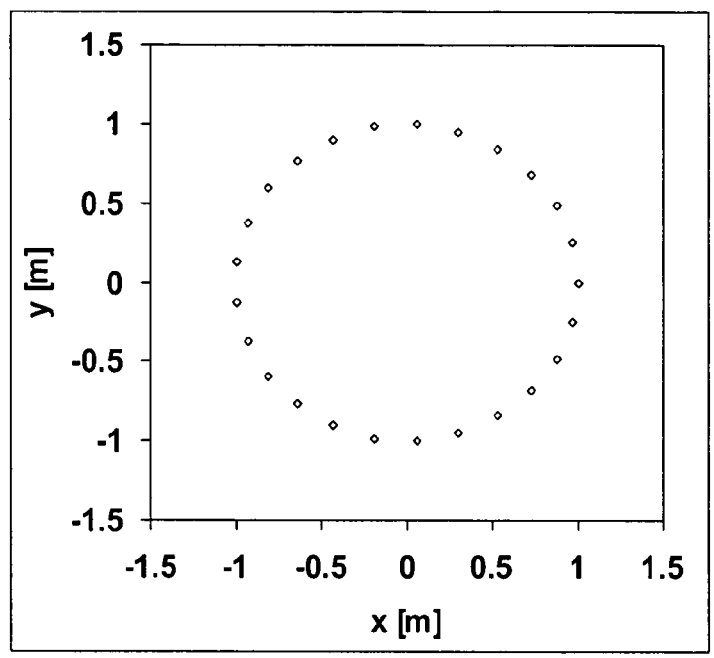
Figure 12:
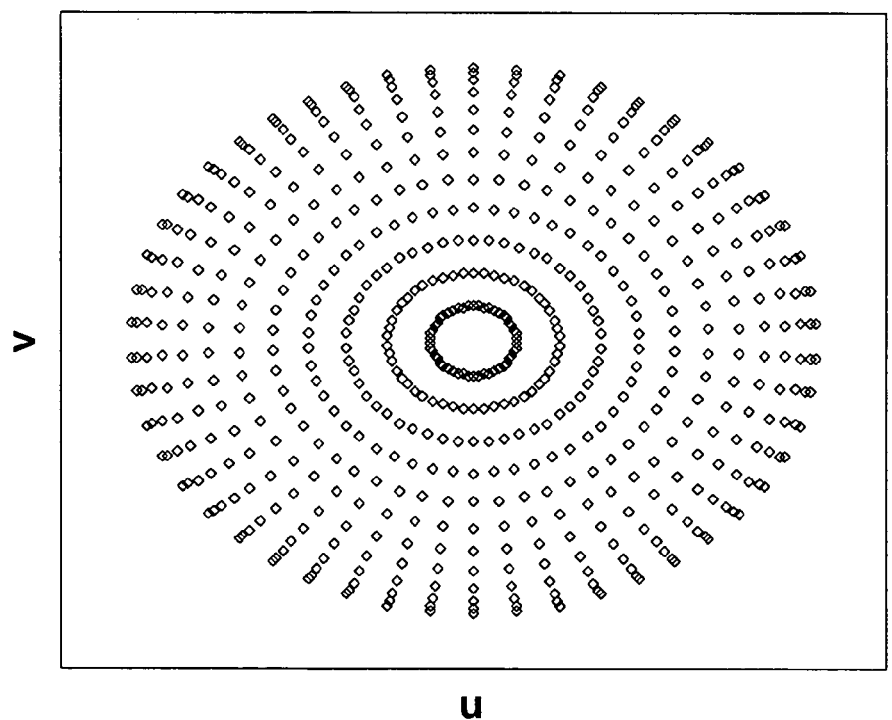

While an array including a fairly large number of detectors may provide efficient and uniform u-v plane coverage, efficient u-v plane coverage may also be achieved for an array that includes a small number of detectors by rotating the array about a fixed axis. If measurements are made 20 times during the rotation of an N element array, the equivalent number of available baseline pairs will be $20 N(N-1)/2$. The use of this technique can either lead to improved image quality or equivalently to a reduction in the number of required detectors in the array for a given image quality. Examples of detector patterns and the resulting coverages in the u-v plane are shown in FIGS. 11a and 11b, respectively, and also in FIGS. 12a and 12b, respectively.

In a preferred embodiment of the present invention, the THz imaging array employs THz detectors manufactured by Picometrix of Ann Arbor, Mich. The Picometrix THz detectors operate as photoconductive devices at room temperature. For these detectors, a gold microfabricated antenna structure is fabricated on top of low-temperature grown GaAs, which is a fast photoconductive material. Output signals are fiber-optically coupled from each detector. For an exemplary set of detector design parameters, the THz imaging array field-of-view is determined by the directionality of the detectors. Detectors field of view can be adjusted from a few degrees to approximately 50° by slightly changes in the design of the THz lens which focuses the THz radiation onto the detector.

Figure 2:
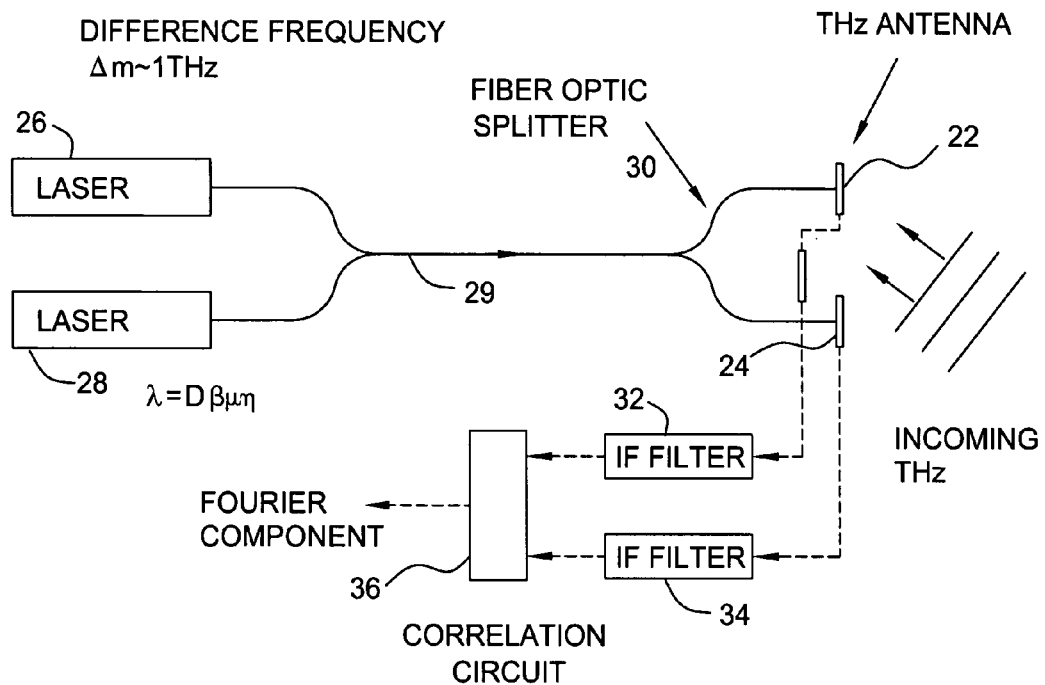
FIGS. 2 and 3 are detailed circuit diagrams showing features of a THz interferometric detector realized in accordance with the principles of the present invention.
Figure 3:
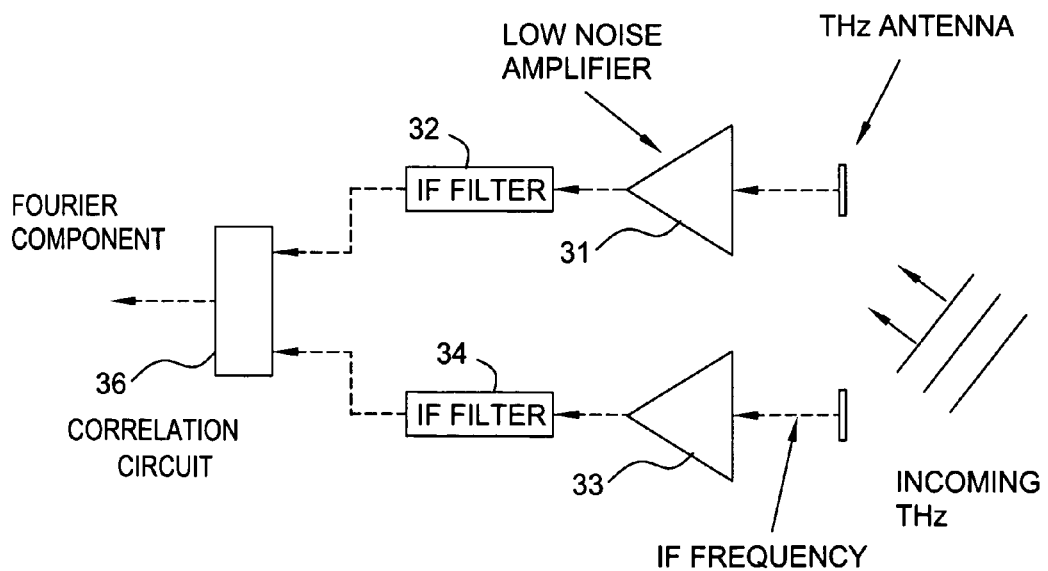

Detector elements in the array can also include a corresponding plurality of semiconductor photomixers and photomixer drivers as shown in FIG. 2. While the system preferably uses a heterodyne photomixing detection technique, it may also use homodyne photomixing detection. High-speed photomixing devices for heterodyne detection are preferably designed to operate at optimum intermediate frequencies. Photomixer drivers including a frequency stabilized tunable optical heterodyne source are coupled to the respective photomixers by a common fiber optic connector or semiconductor waveguide element. Photomixers can be realized by photoconductive devices, whereas the driving means for each pair of such devices is realized by a pair of lasers having a difference frequency suitable for gating each photomixers at a particular rate of interest such as an intermediate frequency. When the incoming THz signals received at each photomixer in a related pair are mixed with the driver output signals at the desired difference frequency, the photomixer output supplies modified signal outputs at intermediate frequencies that are used in the subsequent signal processing to recover the image and identification of the target.

In the illustrative embodiment of a THz imaging receiver shown in FIG. 2, interferometric detection of THz signals is accomplished by an array of fiber-optic coupled, photoconductive antenna detectors. Detectors 22 and 24 form one pair of detectors from the entire imaging array. Incoming THz signals are detected in these detectors by mixing the incoming THz signal with the output signal of the combination of laser beams from two infrared (≈780 nm) lasers 26 and 28. The combination of the laser output signals produces a difference signal in the THz range and is used to "gate" or "turn on" the photoconductive detectors so that the detectors can sample the incoming THz signal from the target. The difference signal is supplied to the detectors via a structure employing an optical combiner, a length of optical waveguide or fiber, and an optical splitter shown collectively as elements 29 and 30. This structure allows the laser signals to be combined and then distributed to a larger number of detectors in a straightforward manner. In this way, one could conceivably use only two infrared laser sources to power every antenna in an N-element interferometric array where a 1×N splitter (star coupler) is used to distribute the difference signal to each of the detectors.

Fiber coupling makes the entire imaging array more robust and reliable. By utilizing detectors that are attached directly to optical fibers, the detectors can be moved relative to each other to provide an adjustable baseline or detector spacing. Optical fiber devices for signal coupling and splitting as well as bulk optic devices and semiconductor devices are contemplated for use in realizing the coupling structure between the detectors and the lasers.

Exemplary lasers 26 and 28 are two narrowband infrared lasers which are used in conjunction with the detectors to detect THz radiation via difference frequency optical heterodyne photomixing. In an example from experimental practice, the lasers are realized by two External Cavity Diode Lasers, (ECDLs), to produce output beams at two different wavelengths of infrared radiation near 780 nm with a linewidth of approximately 5 MHz. When these beams are combined, the resulting difference signal is in the desired THz frequency range (0.1 THz to 2.0 THz). The THz frequency can be tuned by adjusting the wavelength difference of the lasers and thereby the difference frequency of the combined signal.

While homodyne detection of laser mixing in photoconductive antennas has been demonstrated by others, heterodyne detection has only recently been demonstrated in our '683 patent. The heterodyne detection technique improves the sensitivity of the THz imaging array compared to homodyne (DC) detection. Heterodyne detection decouples the THz source at the transmitter from the THz local oscillator (LO) at the receiver. This means that the THz source and LO do not need to be coherent or derived from the same signal source. In the photomixing detection technique, the THz local oscillator signal is provided by mixing of the two infrared laser signals, each at a different wavelength.

In the photomixing structure, one can conceptually think of the mixing of two infrared laser sources as generating a local oscillator (LO) signal within the photoconductive antenna detector element in the imaging array. In this way, an intermediate frequency (IF) signal is produced by the mixing or beating of the local oscillator signal with the received THz signal from the target. An exemplary IF signal produced in this manner can be in the 100–3000 MHz range. The IF signals from output as a result of the heterodyne detection method from each detector can be readily processed using standard electronic components that are generally available in this frequency range.

The relative phase and amplitude of the received THz signal for a pair of detectors (i.e., Fourier component for u-v plane) is determined by correlating the measured intermediate frequency (IF) signal frequencies at the two detectors. The IF signals in a baseline pair are filtered by IF filters 32 and 34. Low noise amplifiers, such as amplifiers 31 and 33, may be inserted in the electrical path between the filters and the detectors to amplify the detector output signal. The pair of filter outputs for a particular baseline is supplied to correlation circuit 36 to produce the necessary Fourier components used for imaging the target. These filtered IF signals can be processed with exactly the same, well-developed correlator technology used in radio astronomy. Correlation is performed on each baseline pair of detector output signals to produce the entire set of Fourier components required for imaging the target.

In the heterodyne mixing technique described above, the incoming THz signal ($\omega_{signal} \approx 1$ THz) received by the individual detector is combined with the local oscillator signal ($\omega_{LO} \approx (1+\delta)$ THz), which differs from the signal frequency $\omega_{signal}$ by a small amount $\delta$. The local oscillator signal, as described above, is produced in the present embodiment of the imaging array by difference frequency mixing of the laser output signal beams. The output IF signal from the detector is produced by mixing to the two THz signals as $\omega_{IF} = \omega_{LO} - \omega_{signal}$. The difference frequency is in the intermediate frequency range and can be electronically processed to retrieve the phase and amplitude of the received THz signal. Other well-known techniques for performing heterodyne mixing and detection are contemplated for use herein. These techniques could even include the use of different local oscillator techniques such as the use of a far-infrared (FIR) laser including a methanol laser or the like. Such techniques may require the use of different detector elements that are responsive to the particular local oscillator signal being used.

It should be noted that by sweeping the local oscillator frequency with a fixed IF frequency, the interferometer is capable of imaging the THz sources at various frequencies. Sweeping of the LO frequency can be achieved by varying the wavelength difference between the two IR lasers. The advantage of sweeping the LO frequency is to enable monitoring of a specific chemical component in the object under study and thereby identify explosives by their spectral characteristics in the THz range. In other words, the heterodyne detection technique in combination with sweeping the local oscillator frequency permits the acquisition of spectral as well as spatial images from the array.

Interferometric Array Designs and Array Platform

As mentioned above, various layout designs and spacings for the antenna or detector elements in the imaging array are contemplated. Several exemplary designs are shown in FIGS. 4, 5, 11, and 12. It is contemplated that other exemplary layout designs for these elements can be realized without departing from the spirit and scope of the present invention.

Figure 4:
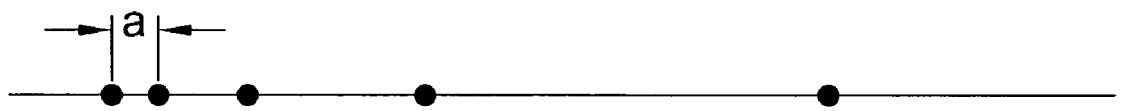
FIGS. 4 and 5 are schematic diagrams of detector element (antenna) layout patterns for use in the THz interferometric detector realized in accordance with the principles of the present invention.

For a given number of detectors N, there are $N(N-1)/2$ possible baseline pair combinations. It is desirable to place the antennas such that there is non-uniform spacing between them in order that the Fourier plane is sampled as completely as possible. A typical in-line arrangement of five antennas, along with the resulting baselines is shown in FIG. 4. A log-periodic spacing is shown for this exemplary structure. An initial separation, a, between a first pair of detectors is established. Successive pairs of adjacent detectors are then separated by distances 2a, 4a, and 9a so that each detector in the in-line array is situated at the following x-coordinate: 0, 1a, 3a, 7a, 16a. In this structure, the baselines between all possible pairs of detectors have the following lengths: 1a, 2a, 3a, 4a, 6a, 7a, 9a, 13a, 15a, and 16a. This provides substantially complete and uniform coverage over the area of interest. This particular array is expected to be combined with a platform or device included in the array controller 16 (FIG. 13) to provide rotation of the array about an axis normal to the imaging array surface through a point at or near the x=0 detector. In an example from experimental practice, a turntable or spindle can be used to realize the necessary rotating platform for the array. Rotation through the full 360° arc is anticipated with samples being taken from the detectors at desired increments such as once every 10°, for example. Other increments are contemplated. But the increment that is chosen should permit the array, when rotated fully, to provide full imaging coverage for the area under observation. For efficient coverage of the Fourier Transform u-v plane, it is understood that the spacing between each detector pair can be varied such that each pair produces a unique spatial Fourier component that is not a harmonic of any other spatial Fourier component. Multiple occurrences of the same detector spacing do not yield any additional imaging information.

As mentioned previously, if the imaging array were on a spinning platform or were allowed to rotate about an axis normal to the array surface in some manner, then the array's rotation relative to the target could be utilized to improve the image quality. If measurements are made at 20 different orientations during the rotation on an N element array, the effective size of the array is increased to an equivalent number of 20N detectors. This improves image quality or, as a tradeoff, can reduce the number of required antennas in the array.

By recording the correlation in the electric fields observed at the various combinations of detector pairs, information as to the spatial distribution of emission of THz signals from the target can be generated. An image is generated from the spatial Fourier components of all the different pair combinations. The quality of the image depends on the coverage of the u-v plane that in turn depends on the arrangement of the detecting elements of the interferometer. The primary concern in designing the configuration of antennas is to obtain coverage of u-v plane uniformly and efficiently over a range determined by the required angular resolution. Efficient u-v plane coverage with a small number of detectors may be achieved using an in-line arrangement of detectors combined with a rotation of the array about a fixed axis. If measurements are made 20 times during the rotation of an N element array, the equivalent number of detectors is 20N. This can either lead to improved image quality or to a reduction in the number of required antennas in the array.

Figure 5:
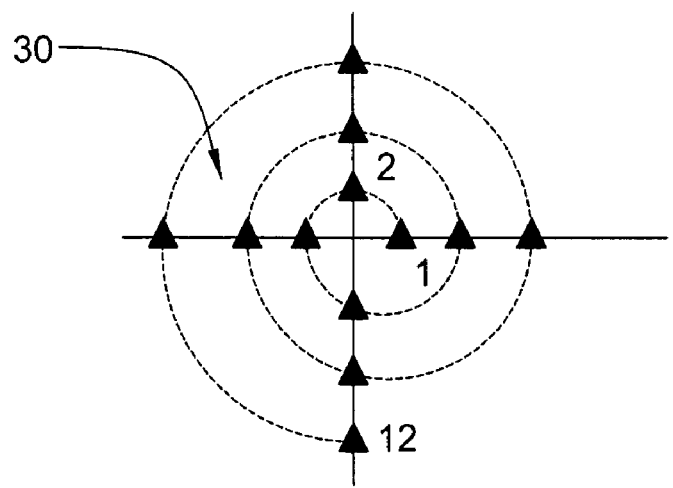

A non-redundant arrangement of 12 detectors as shown in FIG. 5 provides 66 possible Fourier components for every rotational orientation of the array 30. The exemplary array design places a total of 12 detectors along two orthogonal axes intersecting a geometric spiral. Each triangle represents a detector location with each detector being numbered using indices from 1 to 12 in a counter-clockwise fashion. The spacing of detectors in the array shown in FIG. 5 (not to scale) is modeled by the relationship given below as:

$$d_n = a \cdot r_o \cdot b^{n-1},$$

where d is the distance of the $n^{th}$ detector from the origin, a is the spacing constant, $r_o$ is the distance of the first detector from the origin, and n is the index number of the detector. The value b is a constant that describes the rate at which the successive detectors spiral out from the origin. For a particular value of b, the spacing constant a can be used as a multiplicative factor to normalize the overall size of the detector array for different applications. The overall size of the array can be estimated as roughly twice the distance from detector 12 to the origin, where $d_{12} = a r_o b^{11}$. It is contemplated that this array would be rotated at increments through at least 90° to provide reasonably full imaging coverage in the u-v plane. In one example from experimental practice, images are produced from array 30 by rotating the array about the origin to fill in more spatial Fourier components in the u-v plane, adding to the overall resolution of the image. Data is acquired from the array for every 1° of rotational shift over a total of 90°. In this example, the total number of Fourier components realized is 5,940 (66×90) components in the u-v plane.

Using the rotation of the array platform, a target radiating THz signals can be located with only three antennas in the array. In effect, three antennas laid out in a triangular pattern can be used to triangulate the location of a THz source on space. This would allow a computation of the angle of incidence for THz signals from a target. Further improvements can be made by tuning relatively narrowband detectors to various THz wavelengths (as is possible using CW infrared laser excitation). In addition to giving spectral information concerning the THz source, the interferograms at various THz frequencies can be used to improve the spatial resolution or reduce the number of required antennas.

It should be understood that an adjustable baseline design for the detector array allows the possibility that the array can be used to survey a wide area for evidence of explosives very quickly using low spatial resolution. When a particular region in the wide area exhibits spectroscopic signatures of agents of interest, the baseline of the array can be adjusted to examine the suspected narrower area with higher spatial resolution.

It will be appreciated by persons skilled in the art that the spatial resolution of an imaging array is directly proportional to the received THz signal frequency for a particular detector baseline spacing and inversely proportional to the detector baseline spacing for a particular received THz signal frequency. These relationships and the relationship for angular resolution as a function of THz signal frequency and detector baseline spacing are fully disclosed in the above-identified '683 patent and incorporated herein by reference in their entirety.

Figure 6:
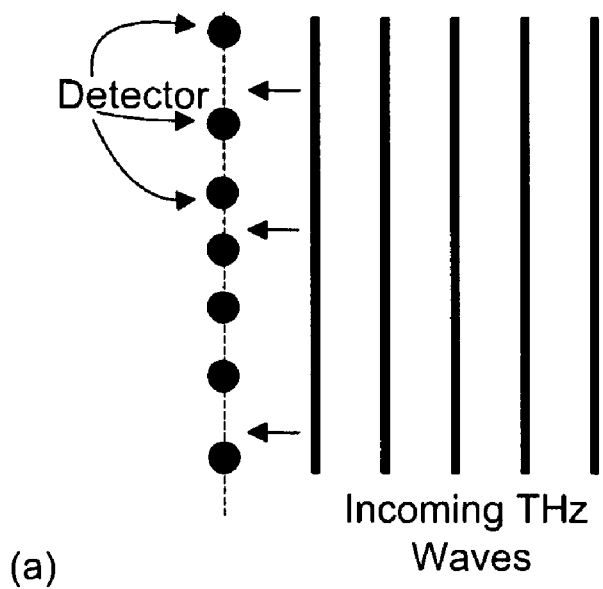
FIGS. 6a and 6b show the received THz signal planar wave front incident on a planar detector array surface.
Figure 6:
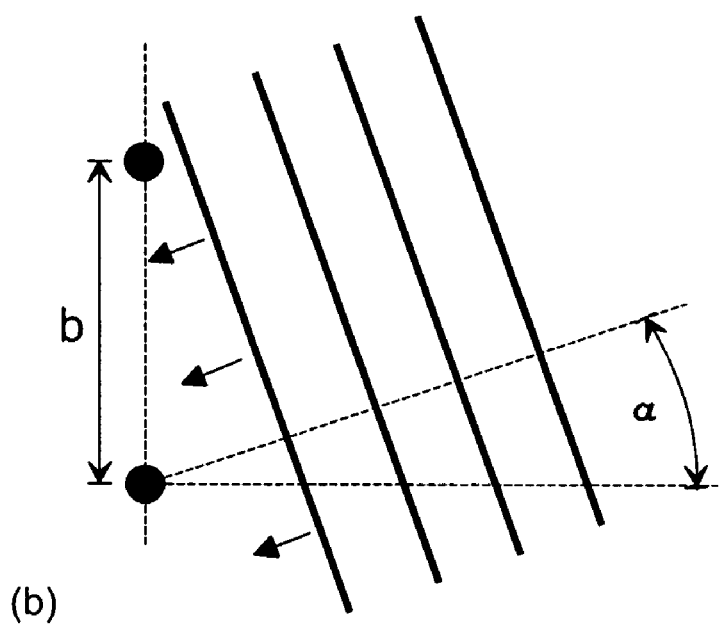

In order to understand the problem associated with imaging in the near-field, consider incoming plane waves from a distant target for which the wave fronts are parallel to a plane (array surface) on which the detector elements of the array are disposed. As shown in FIG. 6a, an individual wave front arrives at all the detectors of a planar array at the same time because the angle of incidence is zero. For a non-zero angle of incidence as shown in FIG. 6b, the time delay between detection of a wave front at two adjacent detectors is related to the distance between the detectors and the angle of incidence. The distance between the detectors is the baseline, b, and the angle of incidence is given as $\alpha$. These figures depict the various situations for signal arrival at an imaging array when the target is in the far field. For the imaging of a far-field object, standard Fourier transforms of correlation of detector pairs gives the reconstructed real image of the object.

Figure 7:
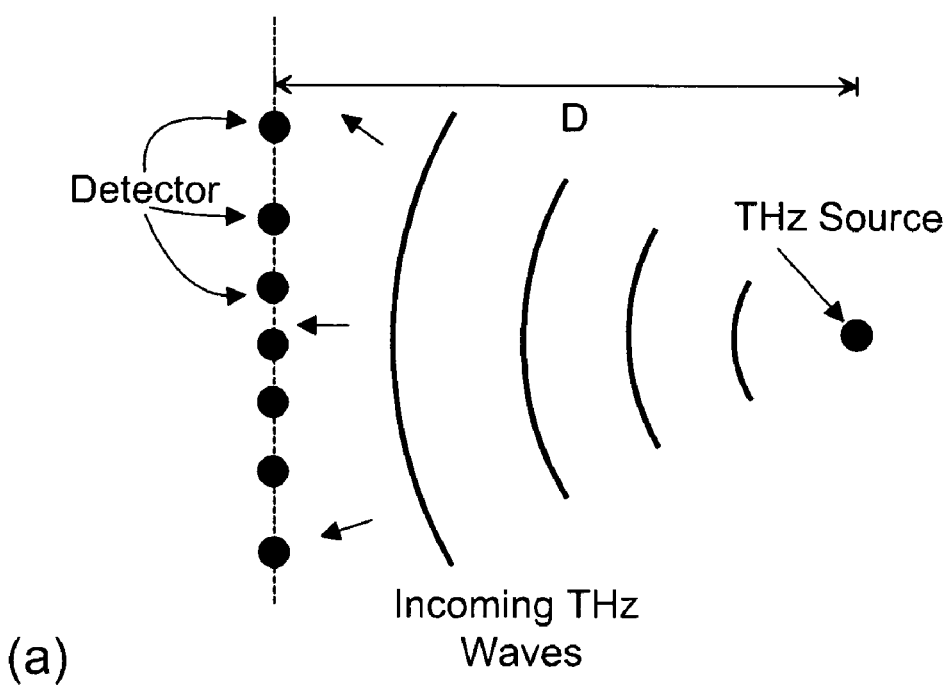
FIGS. 7a and 7b show the received THz signal curved wave front incident on a planar detector array surface and on a curved detector array surface, respectively.
Figure 7:
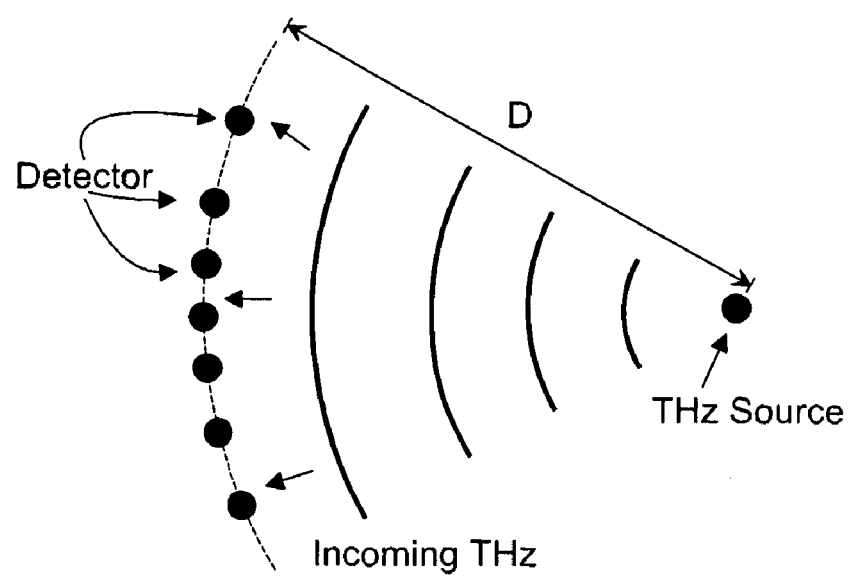

However, if the object to be imaged is not infinitely far away to produce plane wave fronts for the received THz signal, then it must be assumed that the wave fronts are curved as shown in FIG. 7. In this case, when a standard Fourier transform analysis is performed on the received THz signals arriving at the planar array of detector elements shown in FIG. 7a, the reconstructed image will be distorted since the object is too close to the imaging array and the wave fronts are curved.

Figure 8:
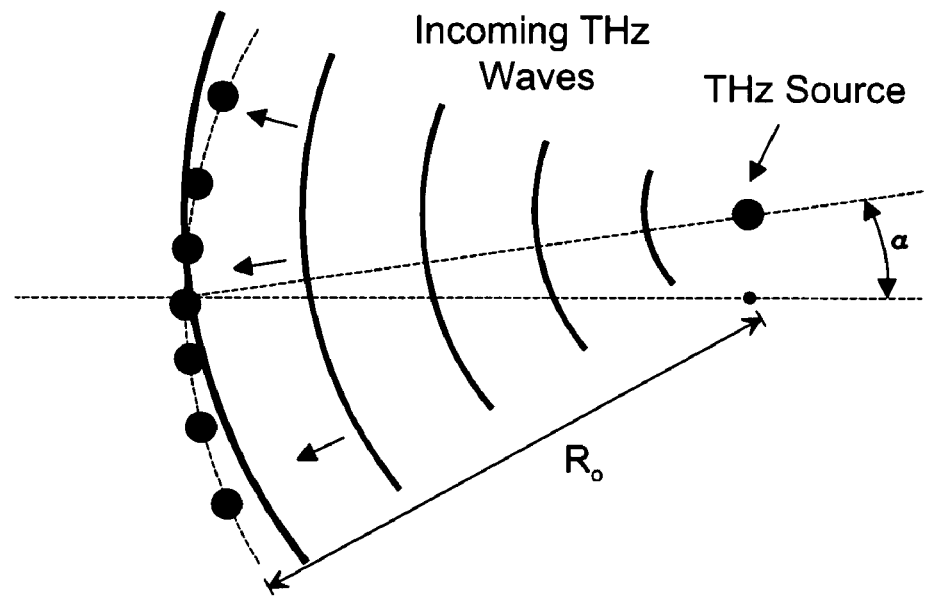
FIG. 8 shows the received THz signal curved wave front incident at an angle α to the surface normal on a curved detector array surface.
Figure 9:
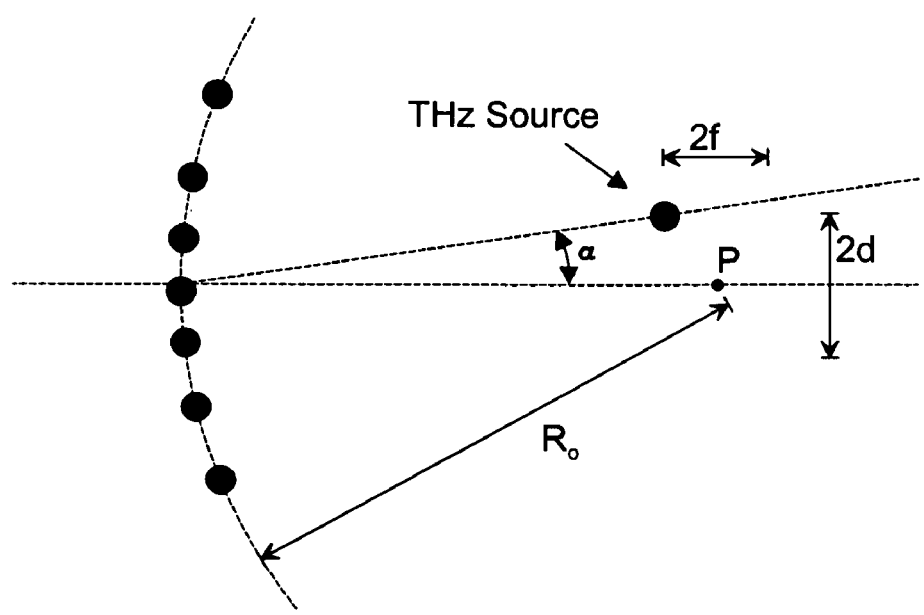
FIG. 9 shows geometric reference points for the curved detector array in FIGS. 7b and 8.

According to the principles of the present invention, when imaging in the a near-field with an interferometric imaging array, the curvature of the imaging array surface and therefore the detector surface is adapted to substantially match the curvature of the wave front. As shown in FIG. 7b, by placing the detectors on a curved surface, the curvature of the wave fronts and detector array are matched. In this case, an individual wave front is detected simultaneously by all detectors. Further time delay correction may be required when the target produces THz signals that arrive at the array at a non-zero angle of incidence $\alpha$. This is depicted for a curved array surface and a curved (near field) wave front in FIG. 8 and is similar to the example depicted for far filed imaging in FIG. 6b. FIG. 9 shows a number of the characteristics for the curved imaging array surface. These characteristics are: an ideal focus point P at the center of curvature of the spherical (actual or synthetic) arrangement of detector elements, a depth of focus ±f around the focus point P, and a lateral range of focus ±d about the focus point P. In FIG. 9, the target is shown as a THz source emitting by reflection or transmission THz signals received at the array at an angle of incidence $\alpha$.

It should be noted that a curved surface of the imaging array of detector elements can be realized by physically shaping the array surface on which the detectors are disposed to substantially match the curved wave front of the received THz signals. The contour of the surface that matches a near field wave front is generally assumed to be spherical although other contours are contemplated. The radius of curvature should ideally be the same as the distance to the target. In applications where targets are expected at multiple ranges, then an average range can be used for the radius of curvature thereby resulting in potentially suboptimal performance for the imaging receiver.

The curved surface can be achieved also by mounting the detectors on a deformable surface or on independently adjustable platforms that can be repositioned in response to a range determination for a particular target. In this way, the curvature and shape of the detector array would be modifiable in response to a determined range to the specific object of interest. Flexible materials are well known in the art. Also, individually adjustable platforms for detector mounting are also well known in the art. Adjustment of the surface or platforms is contemplated as being made by the array controller 16 in response to a range measurement from range detector 15.

Alternatively, an imaging array surface such as a planar surface can be adapted virtually or synthetically to match the curved wave front of received THz signals by adding an appropriate amount of phase delay to the output signals from each individual detector signals during the signal processing of the detected THz wave fronts. This latter technique synthesizes a curved array surface by delaying the detector element signals with respect to each other. Signal delay essentially reshapes the planar imaging array surface into the desired curved surface matching the curved wave front so that contemporaneous signals output from the detector are from substantially the same signal wave front. With respect to the latter technique, it is contemplated that controllable delay can be added at any point in the signal path from the detectors to the processor or correlator. Delay can be realized by using controllably variable delay lines in the electrical circuits between the detectors and the correlator. As mentioned above, the delay can be introduced by the signal processing programs within the correlator itself.

One advantage of using the synthetic or virtual reshaping technique described above is that the same THz receiver with its imaging array can be programmably changed to image objects at different distances, but especially objects in near field applications. While allowing for real-time imaging of an object, this electronic method is easier and cheaper to implement because a planar array surface is simpler to fabricate and can be reconfigured virtually through the use of signal delays to have any imaginable contour.

This technique can be implemented by using a range finder such as range detector 15 (FIG. 13) that determines the distance from the imaging array to the target. In response to a distance measurement from the range finder, an array controller 16, either included within the signal processor or external thereto, sets the individual phase delays for the signals from each detector in the array so that the same wave front of the received THz signal from the target is measured by all the detectors in the array at the same time instant. Range finding apparatus and techniques are well known in the art. Exemplary techniques contemplated for use with the present invention include light detection and ranging (LIDAR) and apparatus similar to that providing the autofocus feature on a still and video cameras.

One method of computing the appropriate time or phase delay is to determine the distance to and approximate location of the target. This will yield the range as well as the incident angle α for the THz signals. From this geometric information, the corresponding delays for each individual detector can be calculated to "focus" the array at the target location. For example, an object 25 m directly in front of the imaging array requires a spherical radius of curvature of 25 m. The appropriate time delay τ can be calculated to be:

$$\tau = \frac{R - \sqrt{z^2 + b^2}}{c},$$

where c is the speed of light, z is the distance to the target normal to the array, b is the separation between a detector to be adjusted and a central detector (requiring no adjustment), and R is the distance to the target from the apparent location of the detector being adjusted. This time delay will "move" the location of the detector from its actual location to an apparent location.

The following description provides further details about the u-v plane and the 2-dimensional Fourier Transform (FT) performed in the processor. In order to introduce the corrections in the near field, it is necessary to discuss the Van Cittert-Zernike theorem which relates the interferometric correlation of detector pairs in the imaging array plane to the amplitude of the radiation at the surface of the object.

Figure 10:
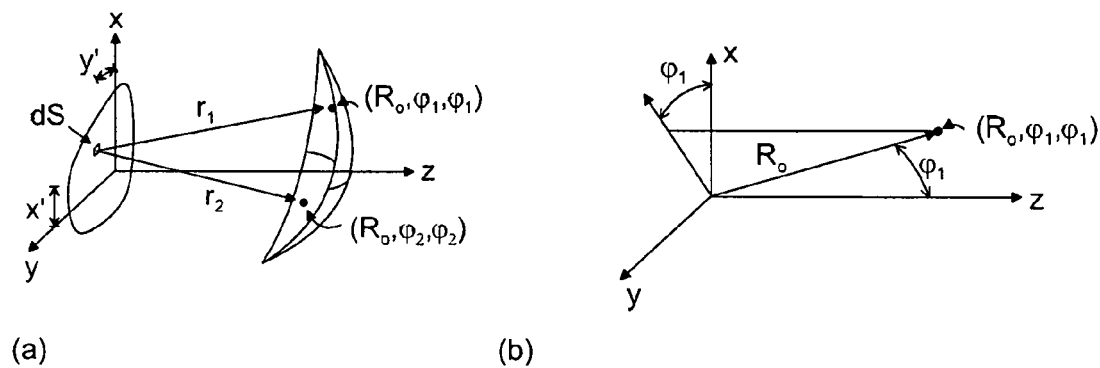
FIGS. 10a and 10b show a target element irradiating a pair of detectors in an imaging array wherein the detectors are disposed on curved surface and where the reference system is shown in spherical coordinates.

A source of radiation in localized over an area dS' (the target) on the x'-y' plane as shown in FIG. 10a. $\psi_o$ is the amplitude of the radiation at source dS'. The source area can be self-illuminating or irradiated from another source of radiation in back (via transmission) or in front (via reflection) of the x'-y' plane. A planar sensor array (not depicted as planar in FIG. 10) is entirely in the x-y plane at position $z=Z_o$. The contribution to the total electric field from the infinitesimal surface dS' at the two detector elements in the imaging array located at $(x_1, y_1)$ and $(x_2, y_2)$ can be expressed as:

$$dE_1 = (\psi_o/r_1)\exp(i\omega t - ikr_1)dS' \quad (1)$$

$$dE_2 = (\psi_o/r_2)\exp(i\omega t - ikr_2)dS' \quad (2)$$

where $r_1$ and $r_2$ are given by $$r_j = [(x'-x_j)^2 + (y'-y_j)^2 + Z_o^2]^{1/2}. \quad (3)$$

In Equations (1) and (2), the electric field is described as a spherical wave whose amplitude decreasing with propagation distance. In addition, it is assumed that the electric fields are all polarized in the same direction so that the electric fields can be treated as scalar quantities. The mathematical form of a spherical wave is a solution to the wave equations derived from Maxwell's equations.

For interferometric detection, the correlation of the electric fields at the various pairs of detectors is calculated. It can be shown that the mutual coherence function of the electric fields at points $(x_1, y_1)$ and $(x_2, y_2)$ can be written as:

$$C_{1,2} = \int_S \frac{\sigma_E(x', y')\exp(ik(r_1 - r_2))}{r_1 r_2} dS', \quad (4)$$

where $\sigma_E(x', y')$ is the time-averaged intensity of the surface at dS', and the integral is over the surface S of the radiating surface (target). This simplified expression also assumes that electric fields, dE, from different locations of the surface are uncorrelated.

Using the expressions in Equation (3), the distances from the target to the two detector elements can be shown to be:

$$r_j = Z_o(1 + (x'-x_j)^2/Z_o^2 + (y'-y_j)^2/Z_o^2)^{1/2}. \quad (5)$$

In the usual approximation, $(x'-x)/Z_0$ and $(y'-y)/Z_0$ are both assumed to be much less than 1 so that the angular extent of the object to be imaged is small. In this limit, $r_1$ and $r_2$ can be approximated as $Z_o$ in the denominator of Equation (4) while the path difference $r_1-r_2$ can be approximated using the first two terms in a binomial expansion as:

$$r_1 - r_2 = \frac{x_1^2 - x_2^2 + y_1^2 - y_2^2}{2Z_o} + \frac{(x_2 - x_1)x' + (y_2 - y_1)y'}{Z_o}. \quad (6)$$

Using the following new variables, $u=k(x_1-x_2)/2\pi$, $v=k(y_1-y_2)/2\pi$, $\xi=x'/Z_o$, and $\eta=y'/Z_o$, the correlation can be cast into the form:

$$C_{1,2}(u, v) = \exp(i\delta) \int_{\infty}^{-\infty} \int_{\infty}^{-\infty} \sigma_E(\xi, \eta) \quad (7)$$
$$\exp(-i2\pi(u\xi + v\eta))d\xi\, d\eta,$$

where $\delta=k(x_1^2-x_2^2+y_1^2-y_2^2)/2Z_o$ is a phase shift resulting from an object in the near field of the planar imaging array. If this phase shift can be neglected, Equation (7) will then relate the coherence function in the antenna plane to the brightness distribution of the source. By a Fourier transform, the brightness distribution (image) of the target can be reconstructed by measuring the coherence function for a given arrangement of detectors in the imaging array. The condition that the phase shift $\delta$ be small can be approximately expressed as $Z_0 \gg b^2/\lambda$, where b is the largest baseline length of the imaging array and $\lambda$ is the wavelength of the detected THz electromagnetic wave. As will be shown below, this condition can be eliminated in the near-field configuration.

The far field form of phase difference between two detectors in a planar array is described below. Two geometric limits are imposed to ensure that the brightness distribution of a source (target) can be imaged through the coherence function in the antenna plane: in the far field $Z_0 \gg (x'-x_j)$, $Z_0 \gg (y'-y_j)$, and $Z_0 \gg b^2/\lambda$. The last condition is the most restrictive with respect to near field imaging. As an example, assume that a 2.5 cm object needs to be imaged from various distances. The angular resolution of a planar array can be approximated as $\theta_{min}=\lambda/b$. At a distance $Z_o$ away, the lateral spatial resolution is $\Delta L_{lat} \cong \theta_{min} Z_o \cong \lambda Z_o/b$. In order to maintain a 2.5 cm lateral spatial resolution at various distances, the maximum baseline for a planar imaging array can be estimated as $b=\lambda Z_o/\Delta L_{lat}$. Using $\delta \sim b^2/Z_o\lambda$ as an estimate of the far-field limit for a planar array, the phase shift limit can be estimated as $\delta \sim Z_o \lambda/\Delta L_{lat}^2$. Table 1 below shows the corresponding maximum baseline required and corresponding phase error to detect a 2.5 cm object from various distances. Note that for the present application, the far-field criteria of $\delta \ll 1$ is never satisfied indicating that the imaging from the interferometric array must include the contributions from the near field.

TABLE 1

Estimated phase error $\delta$ from imaging a 2.5 cm object at various distances using 1 THz radiation.

| | \multicolumn{6}{c}{$Z_o$} |
|---|---|---|---|---|---|---|
| | 5 m | 10 m | 50 m | 100 m | 500 m | 1000 m |
| b | 0.06 m | 0.12 m | 0.6 m | 1.2 m | 6 m | 12 m |
| $\delta$ | 2.4 | 4.8 | 24 | 48 | 240 | 480 |

In the following section, the effect of using a spherical imaging array is described. According to the principles of the present invention, the curvature of the surface of imaging array on which the detectors are disposed is matched to the curvature of a point source thereby eliminating the far-field phase error.

Here the analysis above is modified to correct for the curvature of the wave fronts that are present in the near field. Following FIG. 10, it is assumed that two individual detectors of the spherical imaging array measure an electric field from an element of surface dS' given by Equations (1) and (2). For simplicity, it is assume that the source element dS' lies on a plane at z=0 and detectors can lie at any point on the surface of the sphere with radius $R_o$ as shown in FIG. 10a. The correlation between the two wave fronts at the two detectors can be calculated from Equation (4) as follows:

$$r_j=((R_o \sin \phi_j \cos \phi_j - x')^2+(R_o \sin \phi_j \sin \phi_j - y')^2+(R_o \cos \phi_j - z')^2)^{1/2} \quad (8)$$

Simplification using trigonometric identities yields:

$$r_j=R_O(1-2x' \sin \phi_j \cos \phi_j/R_O - 2y' \sin \phi_j \sin \phi_j/R_O - 2z' \cos \phi_j/R_O + (x'^2+y'^2+z'^2)/R_o^2)^{1/2}. \quad (9)$$

In order to simplify $r_1$ and $r_2$, the near field limit, the same small angle approximations that were used in the far-field case are applied here to yield the path difference as:

$$r_1 - r_2 = x'(\sin \phi_2 \cos \phi_2 - \sin \phi_1 \cos \phi_1) + y'(\sin \phi_2 \sin \phi_2 - \sin \phi_1 \sin \phi_1) + z'(\cos \phi_2 - \cos \phi_1). \quad (10)$$

Substituting the above into Equation 4 and letting $r_1=r_2=R_O$ in the denominator yields:

$$C_{1,2} = \exp(ikz'(\cos\varphi_2 - \cos\varphi_1)) \int\int \sigma_E(x', y') \times \quad (11)$$
$$\exp(ik(x'(\sin\varphi_2\cos\phi_2 - \sin\varphi_1\cos\phi_1) +$$
$$y'(\sin\varphi_2\sin\phi_2 - \sin\varphi_1\sin\phi_1)) \frac{dx' dy'}{R_o^2}.$$

Substituting $\xi=x'/R_o$, $\eta=y'/R_o$, $\delta=kz'(\cos \phi_2 - \cos \phi_1)$, $v=k(y_1-y_2)/2\pi$ and $u=k(x_1-x_2)/2\pi$ Equation (11) assumes the form:

$$C_{1,2} = \exp(i\delta) \int\int \sigma_E(\xi, \eta)\exp(-i2\pi(u\xi + v\eta))d\xi\, d\eta. \quad (12)$$

If the phase shift is small so that $\delta=0$, Equation (12) will then relate the coherence function in the antenna array to the brightness distribution of the source. Assuming that the azimuthal angles of the detectors are not equal, the condition that the $\delta \ll 1$ implies that $kz' \ll 1$ so that the depth of focus (z') of the imaging array is comparable to the wavelength of the THz light (~0.3 mm). It must be pointed out that by choosing the detectors to be arranged in a circle as shown in FIG. 12a with the same azimuth angle forces $\delta=kz'(\cos \phi_2-\cos \phi_1)=0$. The depth of focus as described by z' is restricted by the assumption that $z'/R_0 \ll 1$.

As a mathematical check, the form of the coherence function of a spherical array must be the same for that of a planar array when $R_o \to \infty$ and $Z_o \to \infty$. In the case of the spherical array the phase factor $\delta=kz'(\cos \phi_2-\cos \phi_1) \to 0$ since the azimuthal angles both approach zero as $Z_o \to \infty$. Likewise, the phase factor $\delta=b^2/Z_o\lambda \to 0$ in the case of the planar array.

It has been shown that for remote $TH_z$ detection of targets of interest such as explosives or other $TH_z$ detectable materials, the object is in the near-field regime of an interferometric imaging array. The phase errors can be reduced by designing an interferometric imaging array the detectors of which lie on the surface of a sphere. In the spherical arrangement, the object is in focus within a range of angles and distances to the imaging array. The phase errors of this spherical array arrangement can be minimized by arranging the detectors in a circular pattern. In this case, the phase errors vanish for objects that are close to the symmetry axis of the circular pattern.

Synthetic imaging using an inverse Fourier Transform of u-v components is described below. Simulations of THz signal detection and imaging have been conducted using the geometry depicted in FIG. 10a and employing a curved surface array structure in accordance with the principles of the present invention wherein the detectors are disposed on the curved surface using a spiral layout shown in FIG. 11a and a circular layout shown in FIG. 12a. Extent and uniformity of coverage for these array designs in the u-v plane are shown in corresponding FIGS. 11b and 12b.

Each exemplary imaging array includes 25 individual detectors. The detectors for the circular geometry can be considered to lie on the surface of a sphere with radius of curvature $R_0$ (the center is at the target). The diameter of the circle is determined by the maximum baseline between a pair of detectors and affects the angular spatial resolution for the array. The detector coordinates for the circular geometry of FIG. 12a are evenly spaced around the circle for simplicity although other non-uniform spacings are contemplated. The coordinates for each detector in the spiral array of FIG. 11a are chosen to lie on a spherical surface of radius of curvature $R_0$ as shown in FIG. 10a, where the relationship between rectangular and spherical coordinates is illustrated. The x and y positions of the detectors form a spiral pattern similar to the pattern shown in FIG. 5 and discussed above.

The target point source is located at position (x', y', z') relative to the origin. The distance of the detectors to the z-axis for the spiral array in FIG. 11a vary from 1 cm to 1 m. For the circular array in FIG. 12a, the detector elements are all one meter from the z-axis. The image is generated by calculating the correlation function based on the location of the source and the specified detector positions. The Discrete Inverse Fourier Transform of the coherence function reconstructs the image.

From experimental practice, it has been determined that there is an effect of changing the distance of the target object relative to the imaging array. It is assumed that the target point source is located on the z axis. One observes significant reduction in the reconstructed amplitude of the point source once the source is moved 0.5 m from the ideal focus point of the spiral array. This observation is consistent with the 0.7 m estimated depth of focus for the array. The amplitude as reconstructed by the circular array is unchanged as the point source moves along the z axis, consistent with $\bar{\delta}=0$. This result is not surprising due to the high degree of symmetry of the array wherein the point source is equidistant from every detector on the circular array as it moves along the z-axis.

The peak intensity, noise, and signal to noise ratio (SNR) for displacements in the z and lateral directions have been measured for THz receivers simulated as using these imaging arrays. The noise curves represent the noise that results from sidelobes in the reconstructed images. Noise is defined as the root-mean-square value of the reconstructed intensity with the center peak of the point source image removed. Over the range of lateral and depth displacements between 0 and 1 m, the circular array demonstrates a larger depth of focus while the spiral array exhibits a slight better SNR for the 1 m lateral displacement. For lateral and z displacements, the circular array produces a higher level of noise. This results from the distribution of u-v points relative to the spiral array. The u-v distribution for the spiral array is more efficient for reducing the sidelobes in the reconstructed images. A non-uniform distribution of sensors on the circular array could improve the noise figure.

THz interferometric imaging of centimeter sized objects requires near-field corrections. Near-field aberrations can be minimized by arranging, actually or synthetically, the array detectors to match the curvature of the incoming THz wave fronts. An analysis of the Van Cittert-Zernike theorem for a spherical surface geometry suggests that the near-field aberrations are minimized for either a spiral or circular detector layout within the curved surface imaging array geometry.

While the present invention has been described in terms of specific embodiments thereof, it will be understood in view of the present disclosure, that numerous variations upon the invention are now enabled to those skilled in the art, which variations yet reside within the scope of the present teaching. For example, rotation of the array can be accomplished by a clockwise 180° rotation followed by a counter-clockwise rotation of the same amount. Moreover, instead of using a platform to rotate the array, an optical apparatus such as mirrors or lens combinations could be used to rotate the incoming THz signals while maintaining the array position fixed. Accordingly, the invention is to be broadly construed, and limited only by the scope and spirit of the present disclosure.

The invention claimed is:

1. Terahertz imaging apparatus for examining a region of interest to determine the presence of a specified composition, the apparatus comprising:
    a detector comprising an interferometric array of detector elements arranged at a plurality of spaced apart points on a first surface for detecting terahertz signals emanating from the region of interest, the first surface having a curvature that substantially matches a wave front curvature of the terahertz signals incident thereon from the region of interest; and
    a signal processor for converting detected terahertz signals from the detector into an image of the region of interest from which the presence of the specified composition is determinable.

2. The apparatus as defined in claim 1 wherein the first surface is spherically shaped with a radius of curvature less than 50 m.

3. The apparatus as defined in claim 1 further including means for rotating the array about a fixed axis substantially normal to the first surface.

4. The apparatus as defined in claim 3 wherein the detector elements are arranged in an in-line arrangement.

5. The apparatus as defined in claim 3 wherein the detector elements are arranged along a spiral pattern whose origin substantially coincides with the fixed axis of rotation.

6. The apparatus as defined in claim 2 wherein the detector elements are arranged in a substantially circular pattern.

7. The apparatus as defined in claim 1 wherein the signal processor further includes image analysis means for comparing at least a portion of the imaged region of interest with standard images for the specified composition to determine the presence of the specified composition.

8. Terahertz imaging apparatus for examining a region of interest to determine the presence of a specified composition, the apparatus comprising:
    means for determining a distance from the apparatus to the region of interest;

a controllable detector comprising an interferometric array of detector elements arranged at a plurality of spaced apart points on a first surface for detecting terahertz signals emanating from the region of interest, the controllable detector responsive to the distance supplied by the determining means for controllably deforming the first surface to exhibit a curvature that substantially matches a wave front curvature of the terahertz signals incident thereon from the region of interest; and a signal processor for converting detected terahertz signals from the controllable detector into an image of the region of interest from which the presence of the specified composition is determinable.

9. The apparatus as defined in claim 8 wherein the detector elements are arranged in a substantially circular pattern.

10. The apparatus as defined in claim 8 wherein the first surface is controlled to maintain a spherical shape with a variable radius of curvature less than 50 m.

11. The apparatus as defined in claim 8 further including means for rotating the array about a fixed axis substantially normal to the first surface.

12. The apparatus as defined in claim 11 wherein the detector elements are arranged in an in-line arrangement.

13. The apparatus as defined in claim 11 wherein the detector elements are arranged along a spiral pattern whose origin substantially coincides with the fixed axis of rotation.

14. The apparatus as defined in claim 8 wherein the signal processor further includes image analysis means for comparing at least a portion of the imaged region of interest with standard images for the specified composition to determine the presence of the specified composition.

15. Terahertz imaging apparatus for examining a region of interest to determine the presence of a specified composition, the apparatus comprising:

a controller for determining a distance from the apparatus to the region of interest and for generating a delay signal related to said distance;

a controllable detector comprising an interferometric array of detector elements arranged at a plurality of spaced apart points on a first surface for detecting terahertz signals emanating from the region of interest, the first surface having a contour that is not matched to a shape of wave fronts for the terahertz signals, the controllable detector responsive to the delay signal for controllably delaying output signals from each of the detector elements by corresponding prescribed amounts so that contemporaneous signals output from the detector represent substantially the same wave front from the detected terahertz signal; and a signal processor for converting detected terahertz signals from the controllable detector into an image of the region of interest from which the presence of the specified composition is determinable.

16. The apparatus as defined in claim 15 wherein the detector elements are arranged in a substantially circular pattern.

17. The apparatus as defined in claim 16 wherein the first surface is substantially planar.

18. The apparatus as defined in claim 15 further including means for rotating the array about a fixed axis substantially normal to the first surface.

19. The apparatus as defined in claim 18 wherein the detector elements are arranged in an in-line arrangement.

20. The apparatus as defined in claim 18 wherein the detector elements are arranged along a spiral pattern whose origin substantially coincides with the fixed axis of rotation.

21. The apparatus as defined in claim 15 wherein the signal processor further includes image analysis means for comparing at least a portion of the imaged region of interest with standard images for the specified composition to determine the presence of the specified composition.

* * * * *